United States Patent
Sonnleitner

(10) Patent No.: US 9,550,185 B2
(45) Date of Patent: Jan. 24, 2017

(54) TITER PLATE WITH THIN-FILM-LIGHT SENSOR

(75) Inventor: Max Sonnleitner, Linz (AT)

(73) Assignee: ASMAG-Holding GmbH, Grünau im Almtal (AT)

(*) Notice: Subject to any disclaimer, the term of this patent is extended or adjusted under 35 U.S.C. 154(b) by 610 days.

(21) Appl. No.: 12/514,153

(22) PCT Filed: Nov. 8, 2007

(86) PCT No.: PCT/EP2007/009682
§ 371 (c)(1),
(2), (4) Date: May 3, 2010

(87) PCT Pub. No.: WO2008/055680
PCT Pub. Date: May 15, 2008

(65) Prior Publication Data
US 2010/0202925 A1    Aug. 12, 2010

(30) Foreign Application Priority Data
Nov. 9, 2006 (DE) .................. 10 2006 053 463

(51) Int. Cl.
| | |
|---|---|
| G01N 31/16 | (2006.01) |
| B01L 3/00 | (2006.01) |
| G01N 21/25 | (2006.01) |
| G01N 21/76 | (2006.01) |
| C12M 1/16 | (2006.01) |

(Continued)

(52) U.S. Cl.
CPC ........... B01L 3/5085 (2013.01); G01N 21/253 (2013.01); G01N 21/76 (2013.01); *B01L 3/50851* (2013.01); *B01L 3/50853* (2013.01); *B01L 2200/143* (2013.01); *B01L 2300/023* (2013.01); *B01L 2300/0645* (2013.01); *B01L 2300/0654* (2013.01); *B01L 2300/0663* (2013.01); *B01L 2300/0829* (2013.01); *G01N 21/6454* (2013.01)

(Continued)

(58) Field of Classification Search
CPC .................. B01L 2300/023; B01L 2300/0645; B01L 2300/0654; B01L 2300/0829; B01L 3/5085; B01L 3/50851; B01L 3/500853; B01L 2200/143; B01L 2300/0663; B01L 3/50853; G01N 21/253; G01N 21/76; G01N 21/31
See application file for complete search history.

(56) References Cited

U.S. PATENT DOCUMENTS 6,077,712 A * 6/2000 Livingston .................. 436/91
6,303,316 B1 10/2001 Kiel et al.
(Continued)

FOREIGN PATENT DOCUMENTS

| EP | 1027591 | 8/2000 |
|---|---|---|
| GB | 2369428 | 5/2002 |

(Continued)

OTHER PUBLICATIONS

International Search Report, PCT/EP2007/009682, dated Mar. 27, 2008.

*Primary Examiner* — Jennifer Wecker
(74) *Attorney, Agent, or Firm* — Collard & Roe, P.C.

(57) ABSTRACT

The invention relates to a sample device (1) comprising an array of reaction chambers/wells (3) in a titer plate (2) and a two-dimensional array (10) of thin-film-light sensor elements (12), and each light-sensitive element (12) of the sensor array (10) is disposed directly underneath the individual reaction chamber (3) in order to detect chemical and/or biological reactions.

11 Claims, 3 Drawing Sheets

(51) Int. Cl.
*C12M 1/20* (2006.01)
*G01N 21/64* (2006.01)

(56) References Cited

U.S. PATENT DOCUMENTS

| | | |
|---|---|---|
| 6,686,582 B1 | 2/2004 | Volcker et al. |
| 6,995,348 B2 | 2/2006 | Bradley et al. |
| 7,531,140 B2 * | 5/2009 | Szlosek .......... 422/566 |
| 2002/0004204 A1 * | 1/2002 | O'Keefe ............ 435/6 |
| 2003/0062179 A1 | 4/2003 | West |
| 2003/0127333 A1 * | 7/2003 | Lauks et al. ......... 204/600 |
| 2004/0065806 A1 | 4/2004 | Bradley et al. |
| 2005/0063870 A1 * | 3/2005 | Fukushima et al. ...... 422/82.05 |
| 2005/0176155 A1 * | 8/2005 | Klein et al. ......... 436/163 |
| 2006/0014151 A1 * | 1/2006 | Ogura et al. ......... 435/6 |
| 2006/0105449 A1 * | 5/2006 | Larmer et al. ........ 435/287.2 |
| 2006/0141485 A1 * | 6/2006 | Su et al. ............ 435/6 |
| 2010/0009335 A1 * | 1/2010 | Joseph et al. ........ 435/3 |

FOREIGN PATENT DOCUMENTS

| | | | |
|---|---|---|---|
| GB | 2369428 A * | 5/2002 | ............ G01N 21/05 |
| JP | 50-089092 | 7/1975 | |
| JP | 63-24054 | 11/1994 | |
| JP | 2003517149 A | 5/2003 | |
| JP | 2003329681 A | 11/2003 | |
| JP | 2004532383 A | 10/2004 | |
| JP | 2005527114 A | 9/2005 | |
| WO | 0143870 A2 | 6/2001 | |
| WO | 2006026796 A1 | 3/2006 | |

\* cited by examiner

TITER PLATE WITH THIN-FILM-LIGHT SENSOR

CROSS REFERENCE TO RELATED APPLICATIONS

The present application is a national phase entry under 35 U.S.C. §371of International Application No. PCT/EP2007/009682, filed Nov. 8, 2007, published in English, which claims the benefit of Germany Patent Application No. 10 2006 053 463.8, filed Nov. 9, 2006. The disclosures of said applications are incorporated by reference herein.

The invention relates to a sampling device comprising an array of reaction chambers/wells in a titer plate and a two-dimensional array of light sensor elements.

Many types of devices are used as a means of characterizing samples, including titer plates for example, and the samples are characterized by scanners.

Such scanners use either a movable or displaceable scanner system whereby the samples may remain in a fixed position or the samples can be moved relative to the scanner.

Both cases require some complex machinery, which is all the more complex and hence cost-intensive, the greater the surface area of the sample array to be tested.

Patent specification EP 1 027 591 B1 discloses an optical array system and reading device for micro-titer plates, which permits a massively parallel measurement which massively increases the sample throughput as a result, even in the case of kinematic measurements. A detector array is provided for detection purposes, which may be provided in the form of a CCD array for example, in which case a conventional optical system covering the entire portion is combined with lens arrays across the individual reaction portions. As a result, an image of the entire detected object range is produced true to scale as well as an image or regions of individual wells of the micro-titer plate. By providing an exposure light system, dual use can be made of the optical elements, requiring little effort. The individual imaging areas (wells) are picked up by a telescopic optical reading device and transferred to the CCD-array. Alternatively, it is also possible to use a discrete scanning system to obtain a full reading, permitting a relative movement of the micro-titer plate and mini-lens array, for example a 384-well micro-titer plate, based on four positions one after the other.

Patent specification JP 63 24 054 also discloses a reading device for a titer plate. In the case of the disclosed device, the light emitted from a light source is transported via optical fibers to a row of the titer plate. The light emitted by the optical fibers penetrates the reaction chamber and is picked up and analyzed by a detection system at the rear face. The terminal points of the optical fibers disposed in rows are positioned on the basis of a row of the reaction chamber and the reading operation therefore has to be repeated in steps by positioning the light-emitting device above a respective row of the reaction chamber in order to scan the entire titer plate.

The disadvantage of the known devices is that the reading device and the titer plate are separate components and the light detectors of the reading device are therefore disposed at a specific distance from the reaction chamber, which can lead to scatter losses and can cause the individual reaction chambers to affect one another. Another disadvantage is the fact that the reading device has to be exactly positioned and an optical system must be provided which has to be controlled exactly. Yet another disadvantage is the fact that an additional device is needed in order to determine a radiation intensity which runs the risk of making the reading device dirty when used as intended.

The objective of the invention is to propose a sample device which does not require the use of displaceable mechanical systems in order to characterize the samples, avoids the problem of restricted surface areas of the sample array and also enables even better conclusions to be drawn about the samples. Another objective of the invention is to simplify implementation of the characterization process so that continuously reproducible results can be detected.

This objective is achieved by the invention on the basis of a sample device comprising an array of reaction chambers/wells in a titer plate and a two-dimensional array of thin-film light sensor elements, and each light-sensitive element of the sensor array is disposed directly underneath the individual reaction chamber in order to detect chemical and/or biological reactions.

The solution proposed by the invention totally obviates the need to use moving means in order to characterize the samples, such as those needed with the scanners mentioned above.

The specific advantage with respect to these test methods but also other optical devices resides in the fact that there is absolutely no limit in terms of the surface area of the test surface, in other words the titer plate.

The number of reaction chambers in the titer plate determines the number of light-sensitive elements directly assigned to each chamber so that the two-dimensional extension is of no relevance, at least in terms of imposing a restriction.

However, there is another, even more significant advantage.

The direct assignment of light-sensitive elements, in other words disposing them directly underneath the respective reaction chamber, means that no optical losses occur, such as would necessarily otherwise occur due to the optical systems specific to the unit between the reaction chamber and sensor, for which allowance would then have to be made.

The thin-film light sensor element is a photoactive layer based on organic semiconductors between two electrode layers.

The optoelectronic array comprises rows and columns which represent either an active or a passive matrix array.

This matrix array is preferably read on the basis of pixels, rows or columns.

In one embodiment, the sample device proposed by the invention is equipped with a light source in the form of a two-dimensional array, which enables a full-surface illumination of the reaction chambers/wells on the basis of rows, columns and pixels.

The sample device may also be provided with a control unit, which controls the two-dimensional array of thin-film light sensor elements and/or the light source.

It is of particular advantage if the control unit permits a data exchange via a hard-wired or wireless connection to a computer, PDA, mobile telephone or an equivalent device.

A linear-type disposition of the thin-film light sensor elements represents a special design of a two-dimensional sensor array. A linear layout of the sensor elements has a specific advantage in that the sensor elements can be integrated to a particularly high degree without restricting the amount of space available due to the requisite electrical connecting lines.

A titer plate is preferably formed by a flat support layer in which reaction chambers or so-called wells are disposed in what is usually regular geometric structures. The depth of these reaction chambers is shorter than the thickness of the support layer, as a result of which orifices are provided on the second flat face to enable the reaction material to be introduced into the reaction chambers, and the oppositely lying first flat face has a predominantly smooth and uninterrupted surface. If the light-sensitive elements of the optoelectronic sensor arrays are disposed on this first flat face of the titer plate as claimed, a very intensive contact of the light-sensitive elements with the electromagnetic radiation is guaranteed due to the short distance between the reaction chamber, in particular the base of the reaction chamber, and the light-sensitive element. The short spacing specifically ensures that the electromagnetic radiation generated in the sample chamber or passing through it acts as directly as possible in the light-sensitive element without the measurement result being made weaker or distorted due to diffraction or reflections where media merge in the titer plate or due to external devices. The fact that the optoelectronic sensor array is designed so that each reaction chamber co-operates exactly with a light-sensitive element of the optoelectronic sensor array permits an extremely rapid and reliable evaluation of the reaction in the reaction chamber.

The titer plate is transparent or semi-transparent in the section between the reaction chamber and the light sensor element, at least in the spectral range corresponding to the spectral range of the light emitted by the chemical reaction in the chamber. This spectral range may include the visible optical range but also includes radiation in the infrared and UV ranges. In any event, the light-sensitive elements should be such that they detect the electromagnetic radiation emitted by the reaction in the reaction chamber as efficiently as possible and convert it into an electric signal or a varying electrical characteristic variable. The description also applies to light passing through the reaction chamber and weakened due to the reaction in the chamber.

A particularly advantageous embodiment is achieved if the light-sensitive element of the optoelectronic sensor array is provided in the form of an element selected from the group comprising photodiodes, photo-transistors photo-resistors, because the spectral efficiency of the light-sensitive element can be optimized totally selectively with respect to the electromagnetic radiation to be detected, especially if made from an organic semiconducting material, for example, by means of what is referred to as bandgap engineering. The advantage of optoelectronic light-sensitive elements made from semiconductors is that only a very small amount of energy is needed to detect an incident electromagnetic radiation, and active components may be configured so that incident electromagnetic radiation actively causes an electric output signal without having to supply the component with bias voltage.

Organic semiconductors have another quite specific advantage in that they are particularly energy efficient to use and employ and are environmentally friendly. In particular, no energy-intensive manufacturing processes are needed in order to produce organic semiconductor components, such as high-temperature processing or high vacuum chambers, for example. Furthermore, no complex structuring processes involving the removal of material are necessary, such as photolithographic processes, for example. In particular, organic semiconductor components can be produced by additive processes, for example by means of printing processes such as screen printing, inkjet printing, template printing or stamp printing, for example, and, because of the thin layer thicknesses in the sub-micrometer range, only extremely small quantities of reagents are needed.

In terms of disposal, organic semiconductor components offer specific advantages because there is no need for complex disposal methods. Devices containing organic semiconductor components are therefore particularly well suited for use in disposable items as regards manufacturing and disposal costs and as regards environmental issues. With respect to the sample device proposed by the invention for testing chemical or biological reactions, this has the decisive advantage of offering an inexpensive sample device which can be disposed of without any problems, which means that a new, un-contaminated sample device proposed by the invention is available for every measurement.

However, the claimed design is not just restricted to light-sensitive elements made from organic semiconducting material. In particular, light-sensitive elements from non-organic semi-conducting materials are included, as well as combinations thereof.

In another embodiment, the light source is provided in the form of a plurality of light-emitting elements. The light source is preferably disposed above the sample orifices of the titer plate, in which case the individual elements emit their electromagnetic radiation predominantly in the direction of the sample chambers so that there is no undesirable radiation into adjacent reaction chambers which might distort the measurement.

In another embodiment, the light-emitting element is a light-emitting diode, in which case semiconductor components of this type offer an advantage because the emitted light spectrum can be optimally adapted to the spectral sensitivity of the light sensor and to the anticipated reaction in the reaction chamber. In one claimed sample device, the intensity or course of the reaction in the chamber is determined by evaluating the weakening of the light as it passes through the chamber. The advantage of taking a measurement of through-lighting is that the sample device can be calibrated before the onset of the reaction so that an unambiguous reference value is always available.

In the special case of a two-dimensional array, the light source may also be formed by elements of a linear layout which emit light.

In a preferred embodiment, the light-emitting diode is made from organic semiconductor material.

In another embodiment, at least some parts of the titer plate are made from a material selected from the group comprising glass or plastic material, in which case the plastics may include PMMA, PC, PP, PS, PET, PDMS, COC, for example. The particular advantage of this embodiment is that the titer plate can be made particularly inexpensively and in addition, disposal does not lead to environmental problems. In one advantageous embodiment, the titer plate is transparent or semi-transparent, in which case the transparency need not necessarily include the visible, optical spectral range but may essentially cover only the spectral range relevant to the physical-chemical or biological reaction in the reaction chamber. A transparent or semi-transparent titer plate, at least in the portion through which electromagnetic radiation passes, has an additional advantage because the light sensors can be disposed close to the reaction chambers without the sensor element being at risk from the materials or the reaction in the reaction chamber. Also of advantage in the case of a transparent or semi-transparent titer plate is that the user can easily control and monitor the reaction in the reaction chambers.

Also of advantage is a design whereby the electrodes of the first electrode array are transparent or semi-transparent. The light-sensitive element is formed by a material which is sensitive to light quantums, disposed between two electrode layers, the first and second electrode array. Once the light has passed through the titer plate, in particular the portion underneath the sample chambers, it must also pass through the electrodes of the first electrode array in order to be able to act on the material sensitive to light quantums. For example, in order to direct the charge carrier out of the layer sensitive to light quantums, it is of advantage to use an electrode with as large a surface area as possible. To avoid obstructing the radiation as it passes through, it is of advantage if the electrodes are transparent or semi-transparent, at least in the relevant spectral range. The electrodes may be formed by a thin metal layer, for example, although it would also be possible to use TCOs (transparent conductive electrodes) made from organic materials.

The invention will be explained in more detail below with reference to examples of embodiments illustrated in the appended drawings.

The drawings are schematically simplified diagrams illustrating the following:

FIG. 1a)-d) show several detailed diagrams showing the sample device proposed by the invention:
  a) is a schematic view of one embodiment of the device;
  b) is a detailed diagram of the device proposed by the invention;
  c) is a detailed view of a reaction chamber and a light-sensitive element;
  d) is a diagram showing a section indicated in FIG. 1c);

Figure 1A:
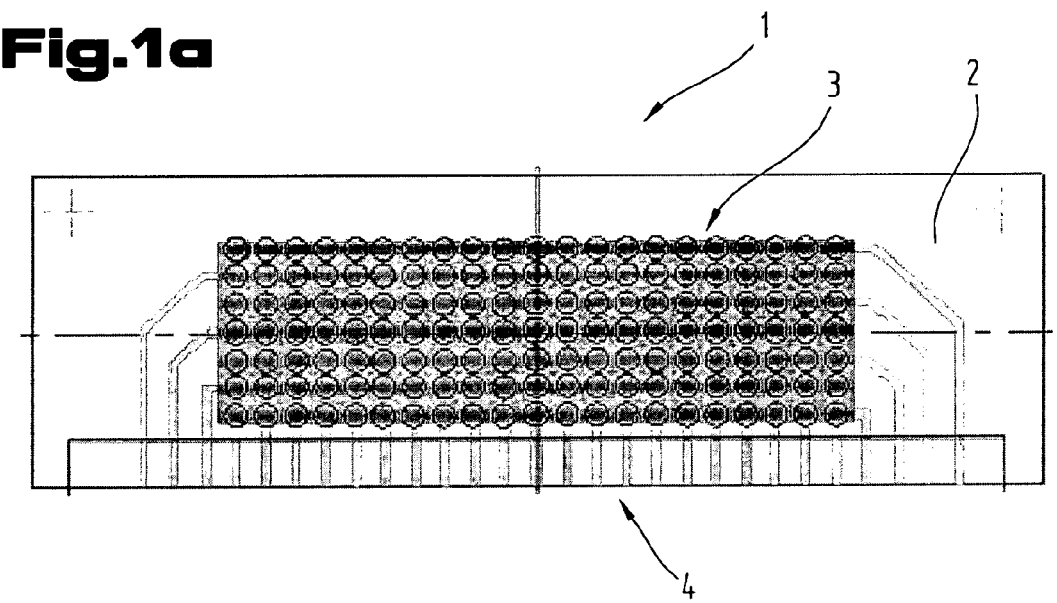

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc,. relate to the drawing specifically cally being described and can be transposed in terms of meaning to a new position when another position is being described. Individual features or combinations of features from the different embodiments illustrated and described may be construed as independent inventive solutions or solutions proposed by the invention in their own right.

All figures relating to ranges of values given in the substantive description should be construed as meaning that they include any and all part-ranges, e.g. the range 1 to 10 should be understood as meaning that it includes all part-ranges starting from the lower limit of 1 and up to the upper limit of 10, i.e. all part-ranges start with a bottom limit of 1 or higher and end with an upper limit of 10 or less, e.g. 1 to 1.7 or 3.2 to 8.1 or 5.5 to 10.

FIG. 1a is a schematic diagram illustrating the sample device 1 proposed by the invention with a titer plate 2, a plurality of geometrically disposed reaction chambers 3 and a plurality of electrodes 4.

Figure 1B:
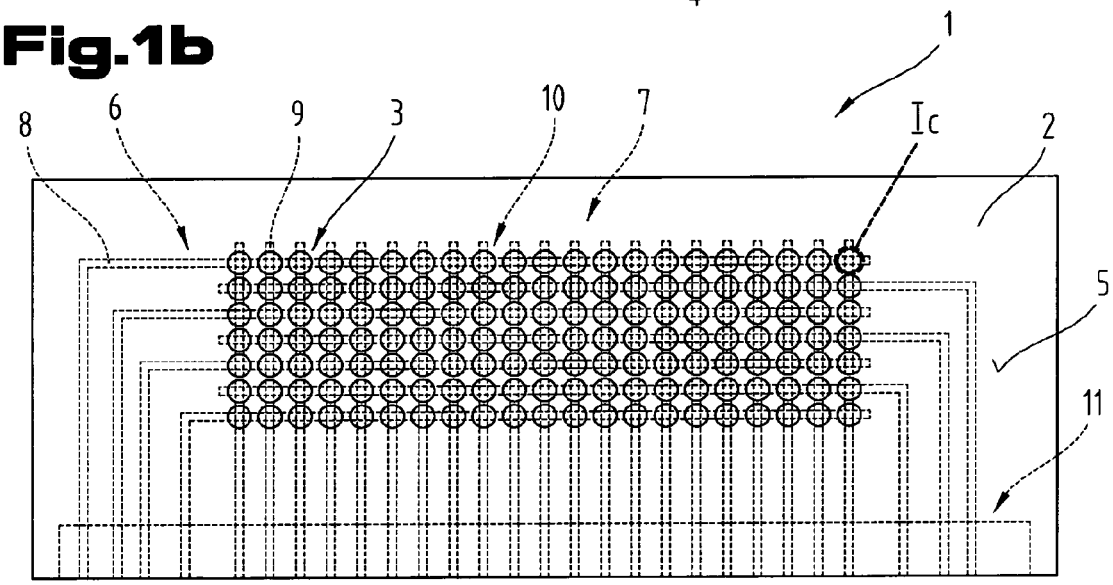

FIG. 1b shows a detailed view of the sample device 1 proposed by the invention. A titer plate 2 comprises a plurality of preferably geometrically disposed reaction chambers 3 or so-called wells, and the reaction chambers are accessible via orifices in the second flat face 5. Disposed on the first flat face lying opposite the second flat face 5 is the optoelectronic sensor array of light-sensitive elements. The thin-film light sensor elements are formed by a photoactive layer, in particular by a material sensitive to light quantums, which is disposed between two electrode layers, in particular a first electrode array 6 and a second electrode array 7. The photoactive layer may be made from a material selected from the group comprising polyfluorene, all PPVs (Poly(p-Phenyl-Vinyl)), phthalocyanine, all P3XTs (X=hexyl, octyl, decyl, dodecyl), PPP (poly-para-phenylene), ladder type PPPs, polypyrrol, although this list should not be construed as exhaustive. The electrodes 8, 9 of the first 6 and second 7 electrode array are disposed in a strip-shaped layout and are rotated relative to one another in their longitudinal extension in the region of the reaction chambers, preferably by 90°. This layout results in a lattice-type arrangement of intersection points of the electrodes of the first and second electrode array, and a photoactive layer, in particular a material sensitive to light quantums, is disposed at least at the intersection point between the electrodes. The electrodes of the first and second electrode array form so-called row and column electrodes so that exactly one light-sensitive element underneath a reaction chamber can be read by selectively activating a row and a column electrode. By scanning all the intersection points in a raster pattern, all the light-sensitive elements of the optoelectronic sensor arrays 10 can be scanned.

The light-sensitive elements of the optoelectronic sensor array 10 are preferably configured as an active matrix array. In the case of a passive matrix, the activation circuit for reading the elements is disposed outside of the sensor array, in which case the individual light-sensitive elements require less space and a higher element density can be achieved. As the elements are being read, cross-talk can occur between the individual electrodes and thus distort signals.

In the case of an active matrix array, one or more transistors is disposed in every light-sensitive element, which can be selectively activated and then emit a sufficiently strong signal to the reading electrode or the reading line, thereby reducing the risk of cross-talk. An active matrix array can be optimized in terms of both small light-sensitive elements and hence a high resolution and in terms of high numbers of pixels.

In the embodiment illustrated, all row and column electrodes are run to a terminal region 11, where they can be connected to an evaluation device. In one advantageous embodiment, however, a control unit may also be provided, which is disposed on or in the titer plate 2 and which assumes control of activating the row and column electrodes and thus the reading of the light sensor element and delivers a measurement value proportional to the reaction at an output.

Figure 1C:
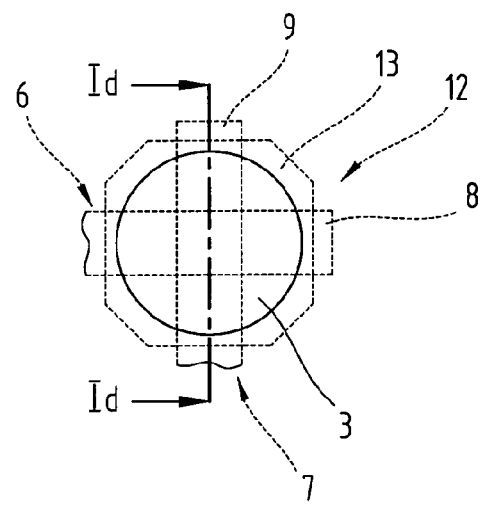

FIG. 1c illustrates a detail from FIG. 1b. Disposed underneath the reaction chamber 3 on the first flat face is a light-sensitive element 12. The light-sensitive element is provided in the form of a material 13 sensitive to light quantums which is disposed between an electrode 8 of the first electrode array 6 and an electrode 9 of the second electrode array 7. The material sensitive to light quantums may be disposed underneath only a part of each reaction chamber, although it is also possible to provide the photoactive layer across predominantly the entire surface between the first and second electrode array. The advantage of a photoactive layer in one advantageous embodiment is that it is electrically conductive only in those portions where light is acting or will induce an electric reaction only where light is acting. This being the case, the photoactive layer may be disposed between the electrode arrays without additional electrical isolation measures being necessary. Incident light on the photoactive layer causes a change in electrical resistance at the light-sensitive element formed by the layer 13 and the electrodes 8, 9, for example a sudden change in the conductivity or also an electric output signal. This change in the characteristic variable is detected by the evaluation device, thereby enabling a conclusion to be drawn about the intensity of the reaction in the respective reaction chamber.

Figure 1D:
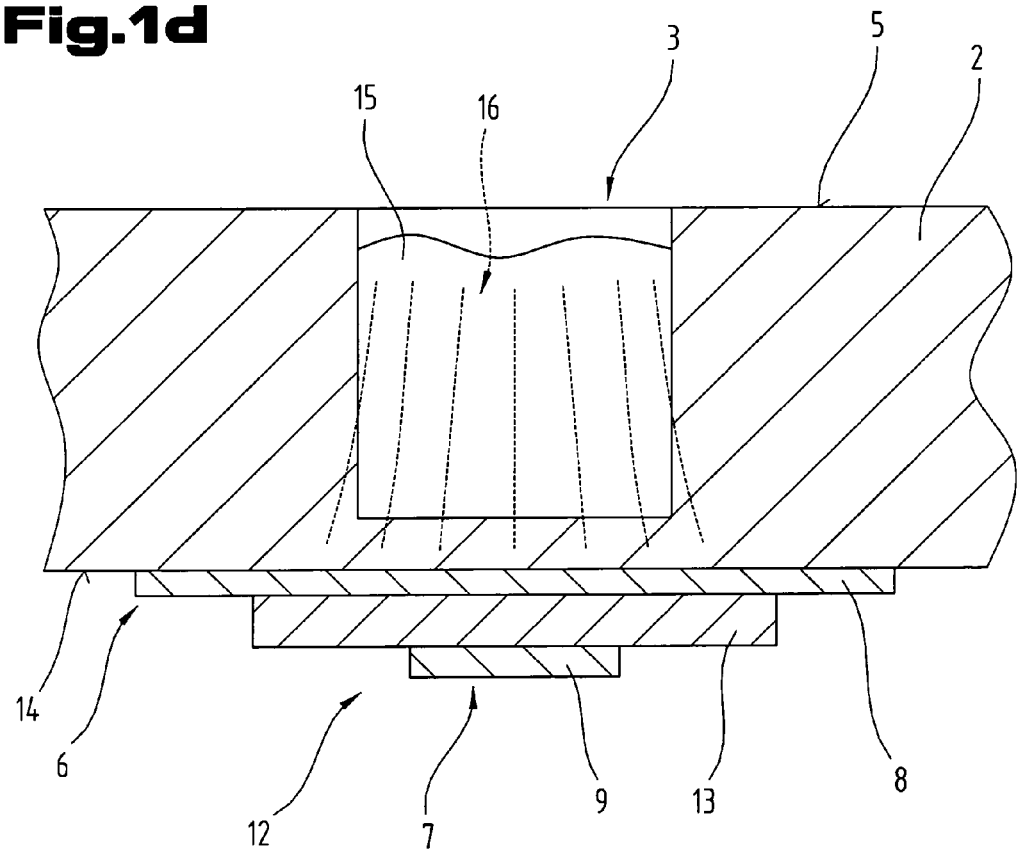

FIG. 1d shows a section through the detailed view illustrated in FIG. 1c. A reaction chamber 3 is disposed in the titer plate 2 so that the volume of the reaction chamber can be accessed through an orifice in the second flat face 5. Disposed on the first flat face 14 of the titer plate is the light-sensitive element 12 provided in the form of an electrode 8 of the first electrode array 6, the material 13 sensitive to light quantums and an electrode 9 of the second electrode array 7. A reaction or sample material 15 is introduced into the reaction chamber 3, leading to a biological-chemical reaction in the chamber. The person skilled in the art will be familiar with the methods of inducing biological-chemical reactions with the aid of titer plates and this aspect will therefore not be described in detail.

The reaction in the chambers 3 can then lead to several effects, which are characterized by the fact that electromagnetic radiation is emitted or electromagnetic radiation penetrating the reaction chambers is weakened, and the electromagnetic radiation preferably falls within the optically visible range, in which case this spectral range is commonly termed as light. In particular, however, the non-visible optical range is also covered, for example infrared and ultraviolet radiation. If light 16 is emitted in the reaction chamber 3 due to the reaction, it is diffused in all spatial directions, including in the direction of the light-sensitive element 12. Due to design features of the rim of the reaction chamber 3, the light can be guaranteed not to impair a measurement in an adjacent reaction chamber. To enable the electromagnetic radiation 16 to penetrate the material 13 sensitive to light quantums, the titer plate 2 and the electrode 8 of the first electrode array 7 must be of a transparent or semi-transparent design, at least in the focal range of the light 16 and at least in the specific spectral range of interest. The titer plate 2 or at least the portions of the titer plate disposed in the focal range are made from transparent plastic, such as PMMA, PC, PP, PS, PET, PDMS, COC, although an embodiment using glass would also be possible. The electrodes of the first electrode array may also be made from thin metal layers, for example, in which case a gold layer 30 nm thick is semi-transparent and a very good electric conductor. In a preferred embodiment, the electrodes may also be provided in the form of TCOs (transparent conductive electrodes), the specific advantage of which is that they are easy and inexpensive to manufacture. In particular, electrodes made from TCOs produced by printing processes may be used, for example inkjet printing, screen printing, stamp printing, thereby requiring no energy-intensive production processes. Since the material sensitive to light quantums is preferably also an organic semiconducting material and organic materials may also be used for the electrodes of the first electrode array 7, each light-sensitive element 12 of the optoelectronic sensor array may be easily and inexpensively produced by means of a printing process. In particular, it is therefore possible to apply the optoelectronic sensor array to a titer plate 2 retrospectively, in particular to print it on. The advantages of organic materials during processing, use and disposal were outlined at various points above.

Since the material of the titer plate 2, in particular the second flat face 14, is not electrically conductive, the electrodes 8 of the first electrode array 6 may be applied directly onto the first flat face 14 without the need for additional electrical isolation features. Given also, that the photosensitive material 13 changes its electrical characteristic variables in the portion acted on by the light only, it may be applied directly to the first electrode array 6. The same also applies when it comes to applying the second electrode array 7 onto the material 13 sensitive to light quantums. These advantageous embodiments enable the optoelectronic array to be applied to the titer plate particularly easily and inexpensively and thereby resulting in an embodiment based on a highly integrated, reliable sample device for detecting a biological-chemical reaction inside the reaction chamber which is particularly suitable for use as a disposable device. Known printing methods are especially suitable for manufacturing the light-sensitive element, such as inkjet printing and screen printing, so that the sensor array can be printed particularly easily and inexpensively onto the titer plate retrospectively, for example by a continuous printing process.

This way of measuring emitted electromagnetic radiation is based on the principle of measuring luminescence and by particular preference, the sample device proposed by the invention is used to determined the reaction intensity based on chemical luminescence. The short distance between the sample 15 and light-sensitive element 12 is of particular advantage when using this measuring method. Especially in the case of chemical luminescence measurements of low concentrations, only very small quantities of light occur and it is therefore particularly important to direct as high as possible a proportion of the light quantums generated onto the sensor.

This proportion is maximized due to the array proposed by the invention, making it possible to take measurements based on chemical luminescence with the highest degree of sensitivity.

In one advantageous embodiment, the sample proposed by the invention may also be used to detect the reaction intensity in the reaction chamber by determining the absorption of electro-magnetic radiation passing through the reaction chambers. To this end, a light source is placed above the second flat face 5 and the light source is formed by a plurality of light-emitting elements, in which case the individual elements are disposed above the reaction chambers respectively. An example of an embodiment based on this design is illustrated in FIG. 3.

The light source may be disposed above the titer plate 2 or integrated in it in such a way that there is unobstructed access to the reaction chamber and there is no risk of the light source becoming dirty or damaged, especially the individual elements, and the individual elements emit their electromagnetic radiation predominantly in the direction of the interior of the reaction chamber 3, thereby preventing any effect on adjacent reaction chambers. However, the light source may also be disposed in a device in which the titer plate is placed or which is placed above the titer plate, for example, thereby ensuring that the individual reaction chambers are selectively illuminated.

Figure 2:
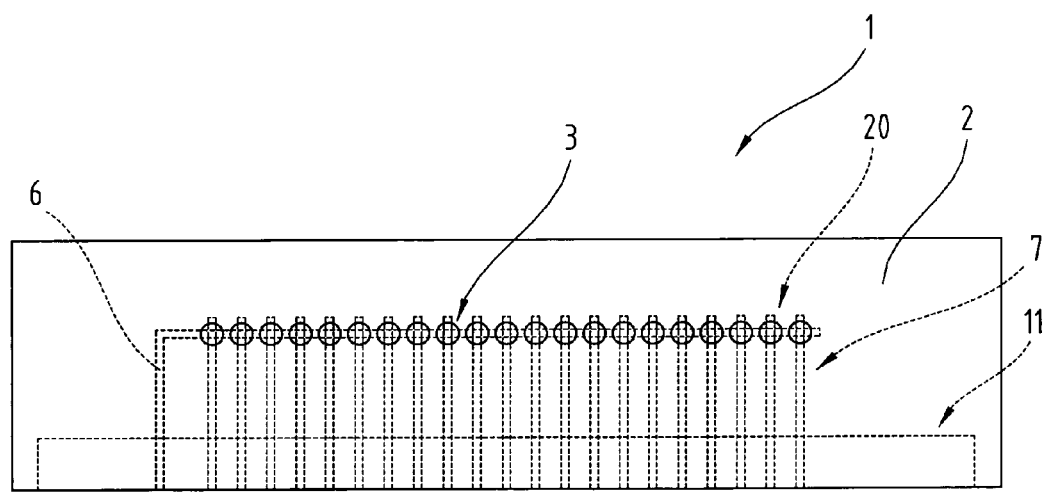
FIG. 2 shows another embodiment of the sample device proposed by the invention.

FIG. 2 illustrates another embodiment of the sample device 1 proposed by the invention. In this embodiment, the titer plate 2 has a linear array of reaction chambers 3, and the light-sensitive elements are also disposed in a linear array underneath the reaction chambers. In order to activate and take a reading from the light-sensitive elements, a one-dimensional electrode matrix is provided, formed by a row electrode 6 and a plurality of column electrodes of the second electrode array 7. The light-sensitive elements are disposed at the intersection points of the first electrode array with the column electrode, formed by a light-sensitive material or a material sensitive to light quantums disposed between the two electrode layers. This material sensitive to light quantums may be provided in only certain parts of the region of the intersection points or may be disposed predominantly across the full surface between the two electrode layers. The electrodes are connected to a terminal region 11 and a control unit is also provided, which assumes control of activating the electrodes and delivers a processed signal proportional to the reaction at an output.

Figure 3:
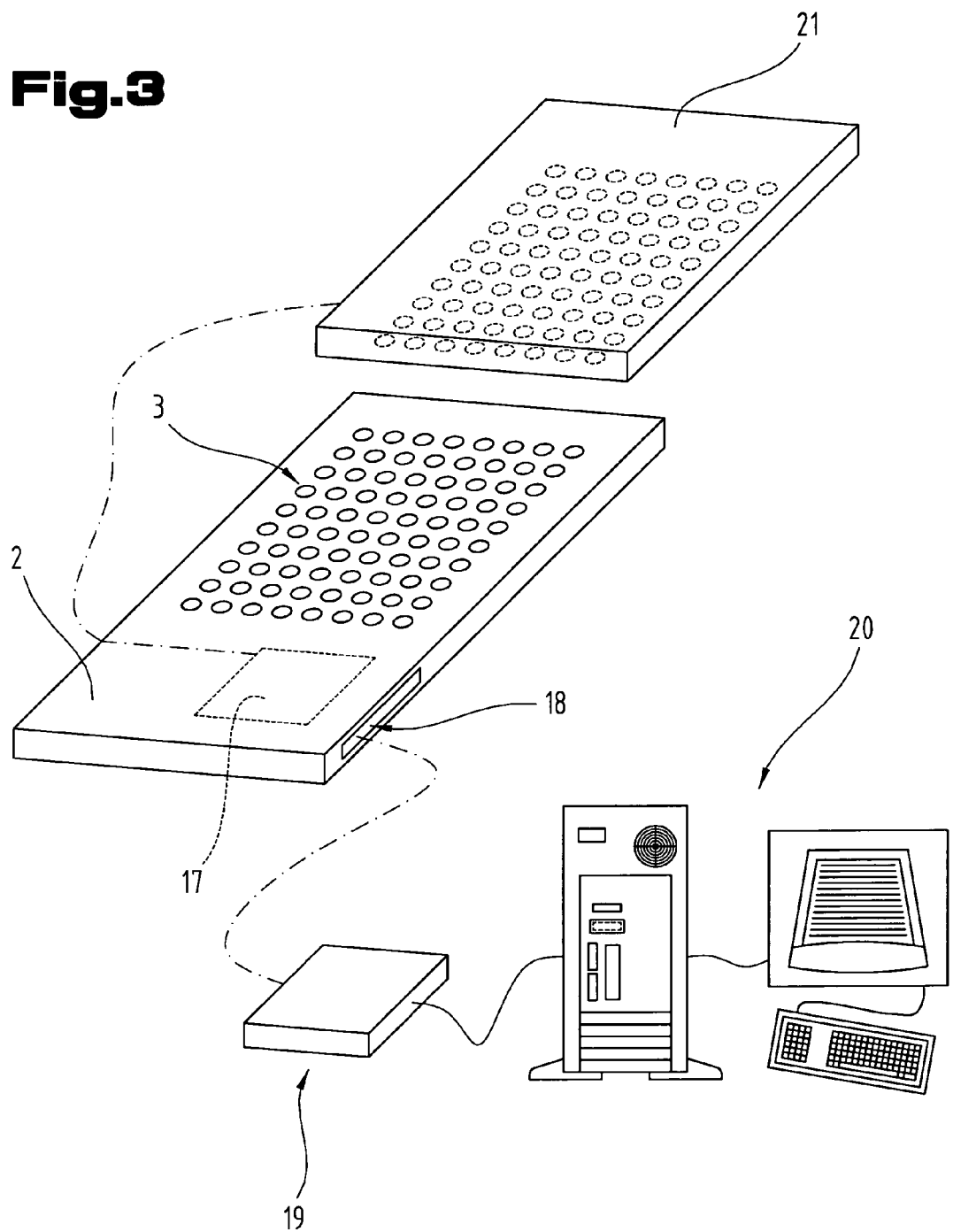
FIG. 3 illustrates an evaluation device for determining the reaction intensity in reaction chambers by means of luminescence and absorption measurement.

FIG. 3 illustrates an example of a device for evaluating the reaction in the chambers of a titer plate. The sample device proposed by the invention comprises a titer plate 2 with a plurality of reaction chambers 3. In one advantageous embodiment, a control unit 17 is provided, which assumes control of activating the light-sensitive elements and supplies a signal proportional to the reaction intensity which is delivered to an interface in a terminal region 18. The terminal region 18 may also have interfaces for transmitting electrical energy. In one advantageous embodiment, a coupling mechanism 19 is coupled with the terminal region and the sample device is connected to a data processing unit 20 as a result. In one advantageous embodiment, however, it is also possible for the sample device proposed by the invention, in particular the control unit 17, to be actively connected to an evaluation device 20 without wires. The data processing unit 20 may be a personal computer, PDA or alternatively a data communication unit designed to transmit remotely.

If, in addition to determining the occurrence of luminescence, it is also necessary to take an absorption measurement, a light source 21 is disposed above the reaction chambers 3. This light source is preferably provided in the form of an array of several light-emitting elements, in which case each element is disposed above an orifice or a reaction chamber so that the electromagnetic radiation is emitted predominantly in the direction of the reaction chamber and hence in the direction of the light-sensitive element disposed behind it. The light-emitting elements of one embodiment are also activated by the control unit. The diagram shows only a schematic illustration of the layout of the light source 21. The light source may be disposed on the titer plate or integrated in it so that the electromagnetic radiation generated is predominantly emitted in the direction of the reaction chambers.

The embodiments illustrated as examples represent possible design variants of the sample device, and it should be pointed out at this stage that the invention is not specifically limited to the design variants specifically illustrated, and instead the individual design variants may be used in different combinations with one another and these possible variations lie within the reach of the person skilled in this technical field given the disclosed technical teaching. Accordingly, all conceivable design variants which can be obtained by combining individual details of the design variants described and illustrated are possible and fall within the scope of the invention.

FIG. 2 illustrates another embodiment which may be construed as an independent embodiment of the sample device in its own right, the same reference numbers and component numbers being used to denote the same parts as those used in FIGS. 1a)-d) above. For the sake of avoiding unnecessary repetition, reference may be made to the more detailed description given above with reference to FIGS. 1a)-d).

For the sake of good order, finally, it should be pointed out that, in order to provide a clearer understanding of the structure of the sample device, it and its constituent parts are illustrated to a certain extent out of scale and/or on an enlarged scale and/or on a reduced scale.

The objective underlying the independent inventive solutions may be found in the description.

Above all, the individual embodiments of the subject matter illustrated in FIGS. 1 to 3 constitute independent solutions proposed by the invention in their own right. The objectives and associated solutions proposed by the invention may be found in the detailed descriptions of these drawings.

LIST OF REFERENCE NUMBERS

1 Sample device
2 Titer plate
3 Reaction chamber
4 Electrodes
5 Second flat face
6 First electrode array
7 Second electrode array
8 Electrode
9 Electrode
10 Optoelectronic sensor array
11 Terminal region
12 Light-sensitive element
13 Material sensitive to light quantums, photosensitive material
14 First flat face
15 Reaction material, sample material
16 Electromagnetic radiation
17 Control unit
18 Terminal region
19 Coupling mechanism
20 Data processing unit
21 Light source, illuminating device

The invention claimed is:

1. A sample device comprising:
    an array of reaction chambers/wells in a titer plate, the titer plate having a first flat face and a second flat face arranged opposite to each other and separated by the thickness of the titer plate, each reaction chamber/well having an opening in the second flat face of the titer plate and extending from the opening in a depth, the depth being less than the thickness of the titer plate, and
    a two-dimensional optoelectronic sensor array of thin-film-light sensitive elements arramged on the first flat face outside the reaction chambers/wells
    wherein each thin-film-light sensitive element of the optoelectronic sensor array is disposed directly underneath the individual reaction chamber in order to detect chemical and/or biological reactions,
    wherein the two-dimensional optoelectronic sensor array comprises rows and columns forming an active matrix array, the active matrix array comprising at least one respective transistor disposed in every thin-film-light sensitive element,
    wherein the thin-film-light sensitive element comprises a photoactive layer based on organic semiconductors between a first electrode array and a second electrode array, and
    wherein the first electrode array is arranged directly on the first flat face.

2. The sample device as claimed in claim 1, wherein the optoelectronic sensor array is read out on the basis of pixels, rows or columns.

3. The sample device as claimed in claim 1, wherein this device is equipped with a light source in the form of a two-dimensional array which enables the reaction chambers/wells to be illuminated on the basis of the full surface, rows, columns and pixels.

4. The sample device as claimed in claim 3, wherein the device comprises a control unit which controls the two-dimensional array of thin-film-light sensor elements and/or the light source.

5. The sample device as claimed in claim 4, wherein the control unit permits a data exchange via a hard-wired or wireless connection with a computer, PDA, mobile telephone or equivalent device.

6. The sample device as claimed in claim 1, wherein the sensor array is provided in the form of a linear layout of thin-film light sensor elements.

7. The sample device as claimed in claim 1, wherein the light-sensitive element is selected from the group comprising photodiodes, photo-transistors, and photo-resistors.

8. The sample device as claimed in 3, wherein the light source is provided in the form of a plurality of light-emitting elements.

9. The sample device as claimed in claim 8, wherein the light-emitting element is provided in the form of a light-emitting diode.

10. The sample device as claimed in claim 1, at least certain portions of the titer plate are made from a material selected from the group comprising glass and plastic material.

11. The sample device as claimed in claim1, wherein the electrodes of the first electrode array are of a transparent or semi-transparent design.

* * * * *

UNITED STATES PATENT AND TRADEMARK OFFICE
CERTIFICATE OF CORRECTION

PATENT NO.        : 9,550,185 B2
APPLICATION NO.   : 12/514153
DATED             : January 24, 2017
INVENTOR(S)       : Sonnleitner It is certified that error appears in the above-identified patent and that said Letters Patent is hereby corrected as shown below:

In the Claims

In Column 10, Line 66 (Line 1 of Claim 3) please change "this" to correctly read: --the--.

In Column 11, Line 18 (Line 1 of Claim 8) after the word "in" please insert: --claim--.

In Column 11, Line 24 (Line 1 of Claim 10) before "at" please insert: --wherein--.

Signed and Sealed this
Seventh Day of March, 2017

Michelle K. Lee
*Director of the United States Patent and Trademark Office*